United States Patent
Goodenough et al.

(10) Patent No.: US 8,348,508 B2
(45) Date of Patent: Jan. 8, 2013

(54) WAVE RAMP TEST METHOD AND APPARATUS

(75) Inventors: David J. Goodenough, Myersville, MD (US); Joshua R. Levy, Salem, NY (US)

(73) Assignee: The Phantom Laboratory, Incorporated, Greenwich, NY (US)

( * ) Notice: Subject to any disclaimer, the term of this patent is extended or adjusted under 35 U.S.C. 154(b) by 282 days.

(21) Appl. No.: 12/953,683

(22) Filed: Nov. 24, 2010

(65) Prior Publication Data

US 2012/0128123 A1 May 24, 2012

(51) Int. Cl.
*G01D 18/00* (2006.01)
(52) U.S. Cl. .......................... 378/207; 378/21
(58) Field of Classification Search ............. 378/21, 378/207; 250/252.1
See application file for complete search history.

(56) References Cited

U.S. PATENT DOCUMENTS

| | | | |
|---|---|---|---|
| 4,055,771 A | 10/1977 | Goodenough et al. | |
| 4,233,507 A * | 11/1980 | Volz | 378/18 |
| 5,164,978 A | 11/1992 | Goodenough et al. | |
| 7,286,631 B2 | 10/2007 | Li et al. | |
| 2003/0122544 A1 | 7/2003 | Parker et al. | |

OTHER PUBLICATIONS

McGraw-Hill Electrical and Electronic Engineering Series, "The Fourier Transform and Its Applications", Bracewell, pp. 69-97, 1965.
Blumenfeld, S.M. & Glover, G., 1981, "Spatial resolution in computed tomography", In: T.H. Newton & D.G. Potts (eds) Radiology of the Skull and Brain, vol. 5; Technical aspects of computed tomography, pp. 3918-3940, St. Louis: Mosby.

* cited by examiner

*Primary Examiner* — Jurie Yun
(74) *Attorney, Agent, or Firm* — Heslin Rothenberg Farley & Mesiti P.C.; Matthew Hulihan, Esq.

(57) ABSTRACT

Method and apparatus are provided for use with a tomographic imaging device. A test object comprising a plurality of angled ramps may be provided to facilitate evaluating performance of the tomographic imaging device. A method for evaluating performance of a tomographic imaging device includes scanning the test object to produce a tomographic slice image and performing analysis on a waveform profile extracted from the image, to determine spatial performance of the tomographic imaging device. A tomographic imaging device may be provided comprising a scanning device and a data processing unit for performing a method of evaluating performance of the tomographic imaging device.

23 Claims, 11 Drawing Sheets

WAVE RAMP TEST METHOD AND APPARATUS

TECHNICAL FIELD

This invention relates to tomographic imaging devices, and more particularly relates to a method and apparatus for evaluating performance of tomographic imaging devices.

BACKGROUND OF THE INVENTION

In the evolving field of tomographic imaging, ever-growing emphasis is being placed on the accuracy of images generated from tomographic imaging devices. In this regard, the ability to more accurately image 3-dimensional volumes is experiencing higher demand. This is especially true in particular applications of tomographic imaging, wherein the advent of greater numbers of multiple slices in a single tomographic scan is seen. The ability of a tomographic imaging device to produce accurate images including accurate 3-dimensional renditions of objects is vital in applications involving volume measurements and 3-dimensional planning of invasive medical procedures.

To evaluate performance of tomographic imaging systems, testing objects (routinely called phantoms) are employed to test and help determine the accuracy of the imaging device, and for calibration purposes. However, phantoms that provide enhanced evaluative value having greater accuracy are needed to keep in-step with this growing demand for greater accuracy and a more complex evaluation of the integrity of tomographic images produced by today's technology. For instance, phantoms that can be used to sample the radial and 3-dimensional extent of a tomographic image, rather than just local in-plane (x,y) and z-axis (thickness) information, are desired. Further desired are phantoms that can produce a visual pattern to aid in the evaluation of the radial and 3-dimensional extent of the image, and/or that are amenable to mathematical analysis of the x, y, and z axis image properties separately and in a simultaneous fashion. Providing such capabilities in a single module test (slice), rather than requiring several module tests (multiple slices) is additionally desired.

BRIEF SUMMARY OF THE INVENTION

The shortcomings of the prior art are overcome and advantages are achieved through the provision of a test object for facilitating evaluation of performance of a tomographic imaging device. The test object includes, for instance, a plurality of angled ramps repeated in a uniform pattern in at least one direction across the test object. The plurality of angled ramps are configured to produce a uniform waveform profile across an image of a tomographic slice of the test object when imaged using the tomographic imaging device.

A method for evaluating performance of a tomographic imaging device is further provided. The method includes, for instance, scanning a test object, extracting from an image of a tomographic slice of the test object a waveform profile of image values, and analyzing the waveform profile of image values to determine spatial performance of the tomographic imaging device.

Tomographic imaging systems relating to one or more aspects of the present invention are also described and claimed herein.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION

Aspects of the present invention can be used in conjunction with various tomographic imaging techniques and devices. In tomographic imaging, a penetrating signal, such as x-rays, are used to image an object in sections, typically cross-sectional "slices". Unlike conventional x-ray imaging techniques, in which a single, 2-dimensional image is formed that images the entire thickness of the object in a single image, a tomographic imaging device can generate one or more images, each corresponding to a particular slice of the object which may be of a considerably smaller thickness than the object itself. When multiple tomographic slice images are created, they may be combined to generate a 3-dimensional volume representative of the entire object.

Aspects of the present invention may be employed with various tomographic imaging techniques, including, but not limited to, x-ray computed tomography (CT) and magnetic resonance imaging (MR). CT includes cone beam, axial, spiral, and multi-slice CT. Additionally, aspects of the present invention may be employed in nuclear medicine tomography, including emission computed tomography such as positron emission (PET) and single photon emission computed tomography (SPECT), as well as nuclear magnetic resonance (MRT) and other emerging hybrid techniques such as SPECT-CT, PET-CT, PET/MRI, as well as others.

The above techniques are set forth for exemplary purposes, and persons having ordinary skill in the art will recognize that these examples do not limit the applicability of the invention only to the examples expressly described herein. For instance, aspects of the present invention may be employed in examples involving other tomographic imaging techniques and their corresponding devices.

Figure 1:
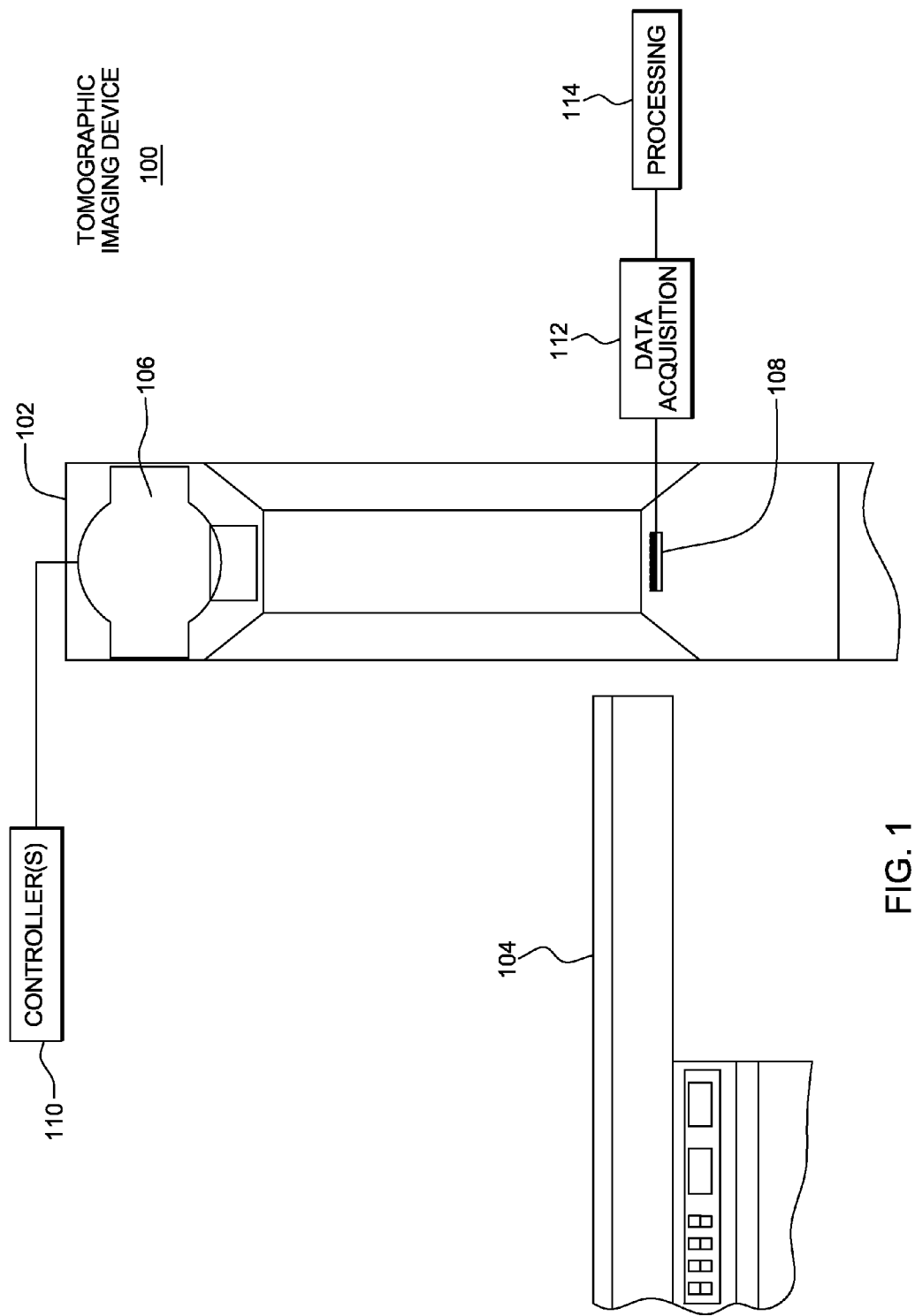
FIG. 1 depicts one example of a tomographic imaging device for use in conjunction with one or more aspects of the present invention.

An example of a tomographic imaging device for use in conjunction with one or more aspects of the present invention is shown in FIG. 1. Again, it should be appreciated that this is provided as just one example of a tomographic imaging device that may be employed in conjunction with the present invention.

FIG. 1 depicts a side view of a tomographic imaging device 100. Tomographic imaging device 100 comprises a scan system 102 and a table 104. Table 104 provides support for, and facilitates the movement of, objects into and out of scan system 102. An object (not depicted) may be positioned partially or wholly within scan system 102 to enable the object to be imaged using tomographic imaging device 100. As depicted in FIG. 1, scan system 102 comprises an x-ray tube 106 and one or more detector(s) 108. X-ray tube 106 may generate x-rays which are directed towards an object when the object is inserted into scan system 102. Detector(s) 108 are positioned substantially opposite x-ray tube 106 and detect x-rays transmitting through the object toward the one or more detector(s) 108. In one example, detector(s) 108 comprise a single detector, however detector(s) 108 could optionally comprise a dual detector arrangement, or a two-dimensional array of x-ray detectors.

In operation, an object, such as a patient in the case of medical imaging, is disposed on table 104. Table 104 and the object disposed thereupon are passed into scan system 102, and x-ray tube 106 generates x-rays to scan the object passing through scan system 102. X-ray tube 106 and detector(s) 108 may be mounted in scan system 102 to a rotary component to allow them to be rotated around the object as it passes through scan system 102, but while remaining in fixed position relative to each other. Table 104 may be inserted into and/or through scan system 102 in a series of steps, with x-ray tube 106 and detector(s) 108 rotating or partially rotating around the object and obtaining a set of data values at each step. Table 104 may then proceed to a next step to repeat the capturing of another set of data values.

Alternatively or additionally, table 104 may be passed continuously through scan system 102 without coming to rest (for example at each step as described above). In this example, x-ray tube 106 and detector(s) 108 rotate continuously around the object and the detector(s) 108 continually collect data signals from x-rays passing through the object, in a technique known as spiral scanning.

Scan system 102 may be in communication with one or more controller(s) 110. Controllers 110 may communicate with scan system 102 for controlling operation of the scan system 102 and/or one or more of its components, such as x-ray tube 106, detector(s) 108 and/or table 104. Additionally, controller(s) 110 may control aspects of the operation of tomographic imaging device 100, such as the power of x-ray tube 106, the rotation of x-ray tube 106 and detector(s) 108 around the object within scan system 102, as well as the movement and positioning of table 104.

Tomographic imaging device 100 also may include one or more data acquisition units 112. Data acquisition units 112 may be in communication with detector(s) 108 to acquire various data from scan system 102, such as signal values generated by the detector(s) 108 and corresponding to detected x-rays. Additionally, data acquisition units 112 may be in further communication with a processing unit 114. In one example, obtained data, such as detected signal values from detector(s) 108, may be passed from data acquisition units 112 to processing unit 114 for performing data processing on the obtained data. For instance, processing unit 114 may include components for interpolation processing and/or back-projection processing, depending on the form of tomography employed, to generate one or more images of a tomographic slice of the object being scanned. Data processing units 114 may be in communication with other devices such as a display device (not pictured) for displaying images, such as images of one or more tomographic slices of an object being scanned. Although controller 110, data acquisition units 112, and processing unit 114 are depicted to be separate components, it should be understood that these may be combined into one or more components of tomographic imaging device 100.

Data processing, such as data processing performed by processing unit 114, may be performed using program logic associated with one or more programs executing on one or more processors of processing unit 114. In on embodiment, the one or more programs are provided as part of a scanner software package provided with the tomographic imaging device, such as by a manufacturer of the tomographic imaging device. Alternatively or additionally, data processing may be performed using independent data processing programs, such as a separate software package executing either on the processing unit 114 or executing on a separate processing unit but using data generated via data acquisition units 112.

As noted above, it is important to ensure the reliability and functionality of tomographic imaging devices. For instance, in medical imaging—a popular application of tomographic imaging—the integrity of the images is important for proper diagnosis and treatment of individuals. Therefore, it is desirable to perform tests from time to time that evaluate performance of the imaging device to assess accuracy of the device and for calibration purposes. To perform such tests, objects such as test phantoms are scanned using the device and the images generated therefrom are then evaluated.

Figure 2:
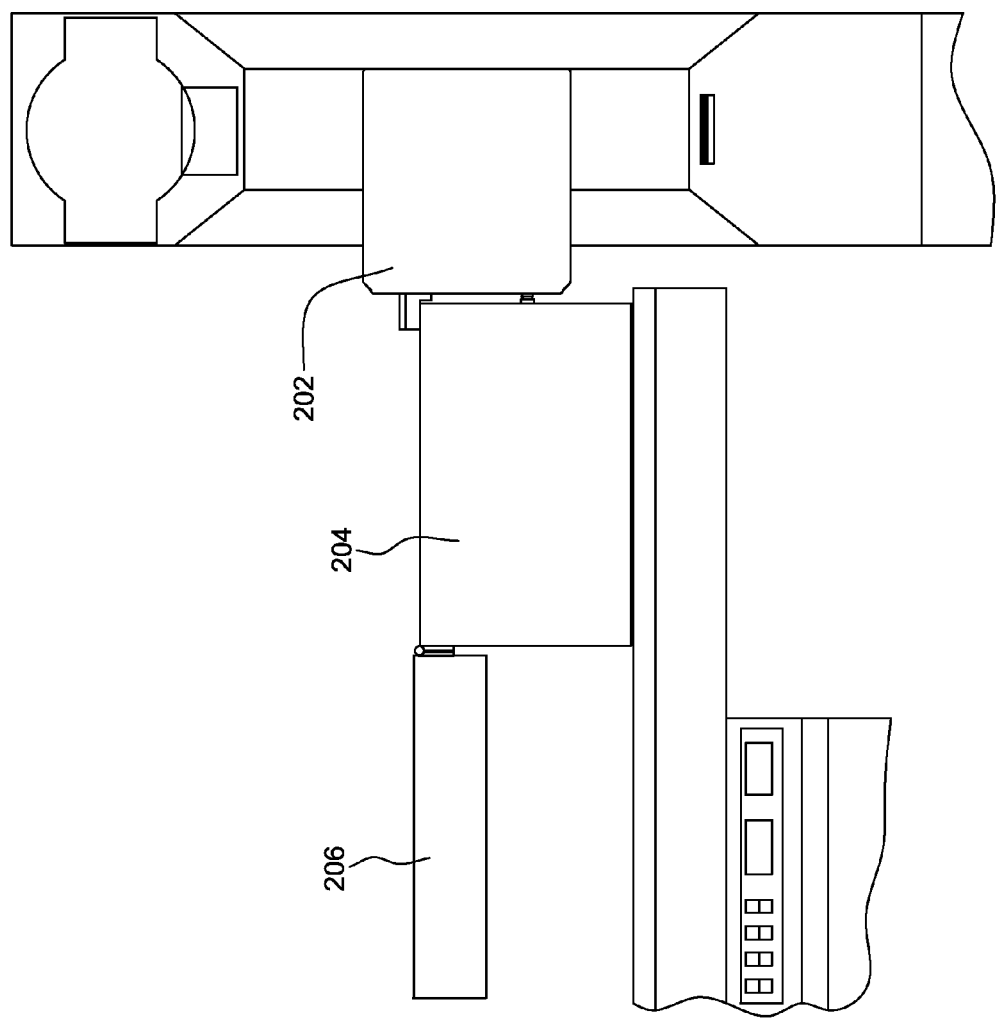
FIG. 2 depicts one example of a tomographic imaging device in use with a test phantom according to one or more aspects of the present invention.

FIG. 2 depicts one example of a tomographic imaging device in use with a test phantom according to one or more aspects of the present invention. Shown in FIG. 2 is a tomographic imaging device 200, for instance, in one example, tomographic imaging device 100 of FIG. 1. FIG. 2 further includes a test phantom 202 partially inserted into the scan system. Test phantom 202 in this example is positioned in a location typical of when a test scan is performed to test tomographic imaging device 200. Test phantom 202 is shown mounted to a mounting case 204 which is used to support test phantom 202 as it is inserted into the scan system of tomographic imaging device 200, and which also provides a base for adjustment and reproducibility of test phantom position. Additionally, a counter weight 206 is attached to mounting case 204. Counter weight 206 may offset the weight of test phantom 202 to prevent mounting case 204 from tipping. During testing of tomographic imaging device 200, mounting case 204 is positioned on the table (see 104 of FIG. 1) and test phantom 202 may be imaged by tomographic imaging device 200. Further details of a test phantom, such as test phantom 202, are provided below with reference to FIG. 3.

Figure 3:
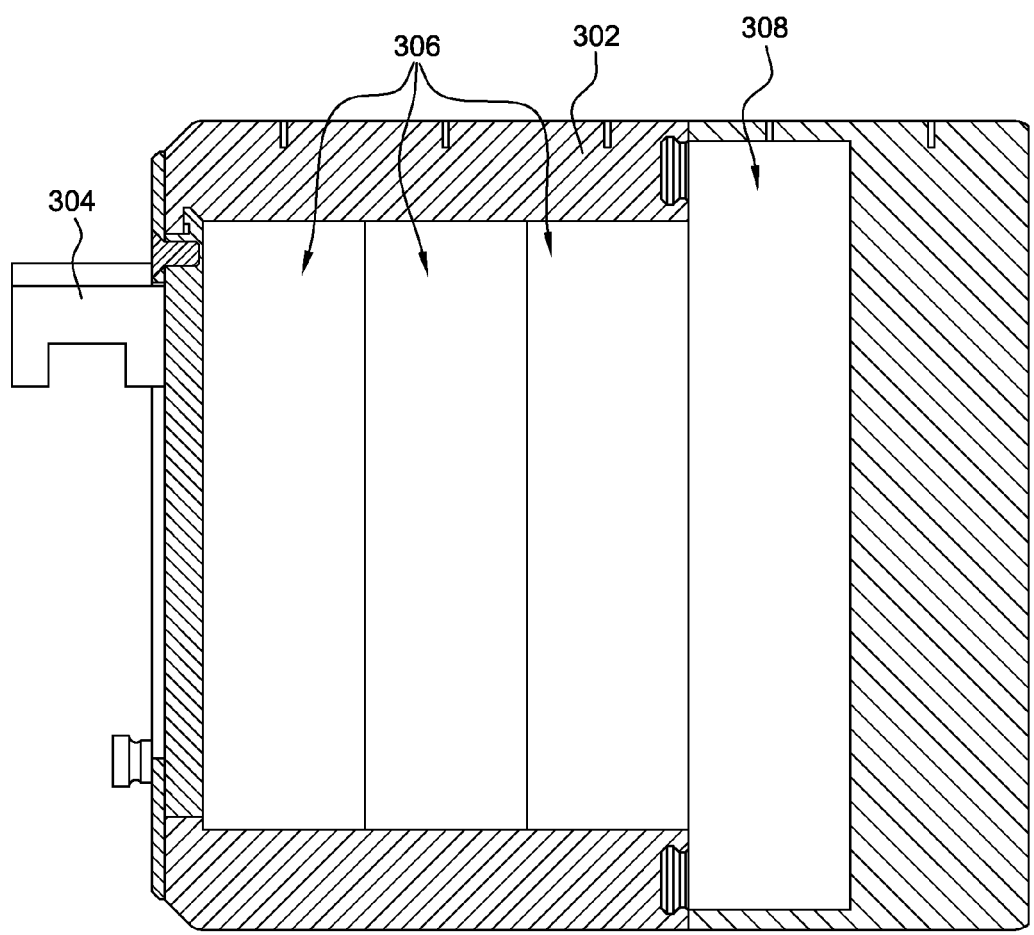
FIG. 3 depicts one example of a test phantom according to one or more aspects of the present invention.

FIG. 3 depicts a cross-sectional view from the side of one example of a test phantom according to one or more aspects of the present invention. Test phantom 300 comprises housing 302 and mount 304 for mounting on a mounting case (see 204 of FIG. 2). Depicted within housing 302 are one or more inserts 306. Inserts 306 may comprise one or more test structures used in testing a tomographic imaging device. Inserts 306 may, in one embodiment, be removable and/or replaceable. In this manner, inserts 306 of test phantom 300 are changeable, which provides test phantom 300 with the flexibility to be adapted depending on the particular tests being performed. For instance, test phantom 300 may be usable to test a variety of different characteristics of a variety of different tomographic imaging systems using different test structures by providing the test phantom with the appropriate inserts as the case may be.

Test phantom 300 also comprises a test object 308 in accordance with one or more aspects of the present invention, and described and depicted in further detail below with reference to FIGS. 4A-4D. In one embodiment, test object 308 may be an insertable object, much like inserts 306.

Figure 4A:
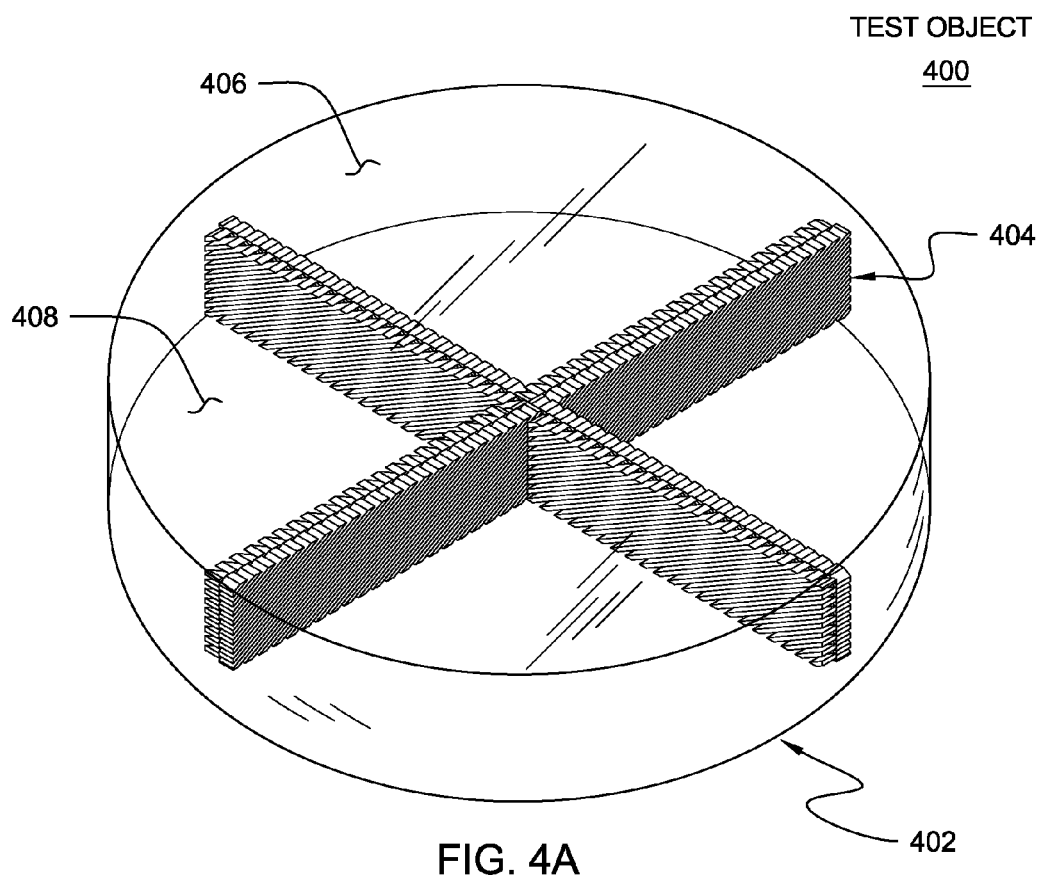
FIGS. 4A-4D illustrate an example of a test object in accordance with one or more aspects of the present invention.

FIGS. 4A-4D illustrate an example of test object (such as test object 308 of FIG. 3) in accordance with one or more aspects of the present invention. FIG. 4A depicts an isometric view of such a test object. Depicted therein is test object 400, which includes, in this embodiment, disc 402 and angled ramp structure 404 embedded therein. Disc 402 comprises a first surface 406 and an opposing second surface 408, with angled ramp structure 404 disposed therebetween. In the isometric view presented, first surface 406 is depicted above angled ramp structure 404, and second surface 408 is depicted below angled ramp structure 404. In one embodiment, first surface 406 is parallel to second surface 408, and both first surface 406 and second surface 408 are flat planar surfaces. Disc 402 could be, in one example, an insertable module much like inserts 306 (FIG. 3).

In this example, test object 400 is a solid cast with angled ramp structure 404 embedded within disc 402. Disc 402 and angled ramp structure 404 may comprise different materials such that when test object 400 is imaged using a tomographic imaging device, features of the disc are distinguishable from features of the angled ramp structure in the images created. For instance, in one embodiment, disc 402 may comprise a material having a different absorption density than a material of the angled ramp structure 404, so that the disc material interferes with a penetrating signal of the tomographic imaging device differently than does the material of the angled ramp structure 404. In one example, disc 402 of FIG. 4A comprises a urethane material and angled ramp structure 404 comprises a different material, such as a thermoplastic type material sold under the trademark Delrin® available from E. I. du Pont de Nemours and Company (DuPont). The difference in signal absorption characteristics in the materials of the test object facilitates evaluating performance of the tomographic imaging device, as will be explained in greater detail below. Further details of angled ramp structure 404 are described with reference to FIGS. 4B-4D.

Figure 4B:
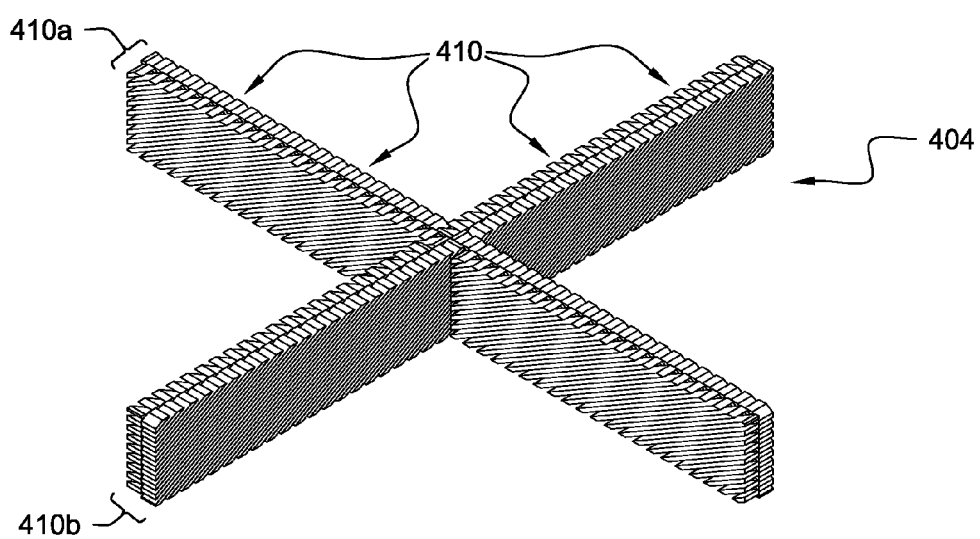
Figure 4C:
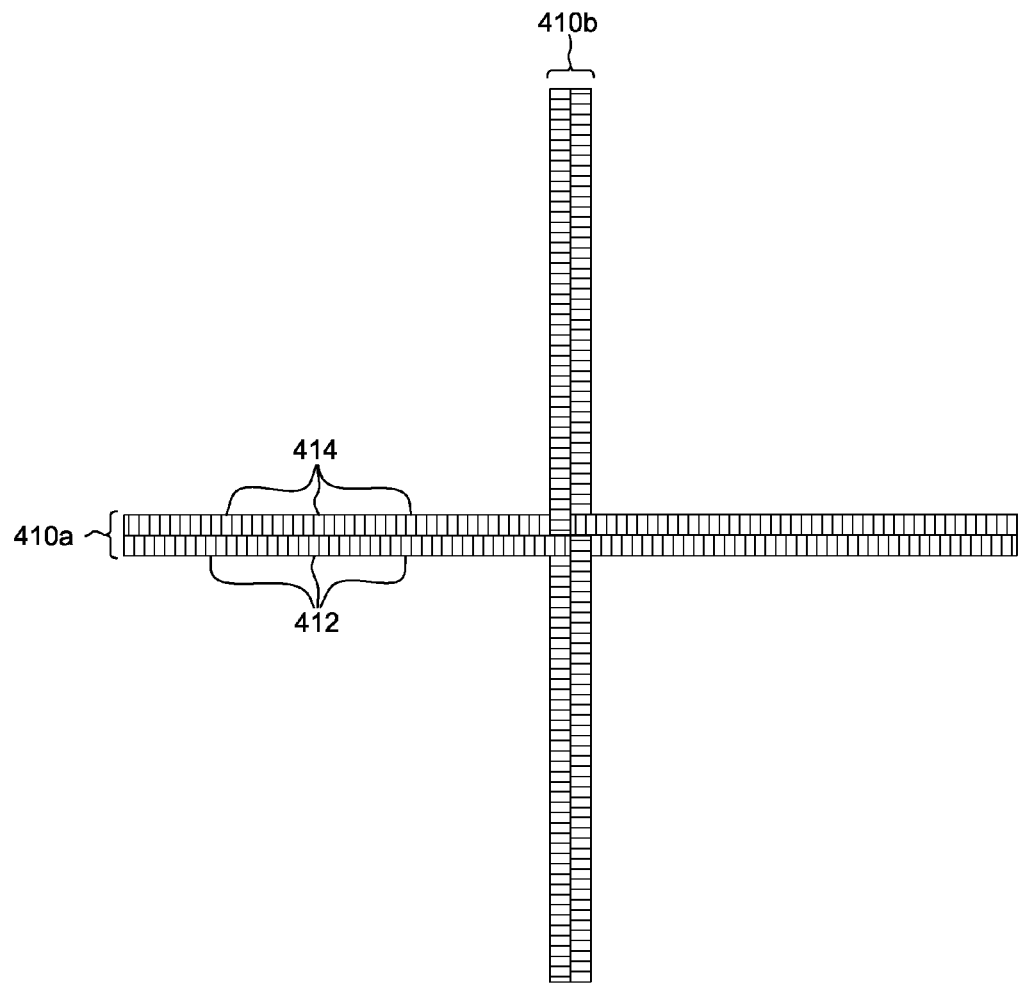

FIG. 4B depicts an isolated view of an angled ramp structure 404 of FIG. 4A. Angled ramp structure 404 comprises a plurality of angled ramps 410. The plurality of angled ramps 410 may each comprise, for instance, a single solid structure of uniform thickness. In this embodiment of angled ramp structure 404, the plurality of angled ramps 410 form a generally cross-like structure comprising a first plurality of angled ramps 410a and a second plurality of angled ramps 410b. In one embodiment, the first plurality of angled ramps 410a extend across test object 400 in a direction perpendicular to the second plurality of angled ramps 410b. This can be more clearly seen in FIG. 4C, depicting a top view of angled ramp structure 404.

In one embodiment of the test object, a plurality of the angled ramps of angled ramp structure 404 comprises a first set of angled ramps and a second set of angled ramps. Referring to FIG. 4C, a first set of angled ramps 412 of the first plurality of angled ramps 410a is depicted adjacent to a second set of angled ramps 414 of the first plurality of angled ramps 410a. Together, the first set of angled ramps 412 and the second set of angled ramps 414 form the first plurality of angled ramps 410a extending across test object 400.

In accordance with an aspect of the present invention, angled ramps 410 may be configured to produce an ideally uniform repetitive waveform profile across an image of a tomographic slice of the test object when imaged using a tomographic imaging device. This is described in further detail below.

Figure 5:
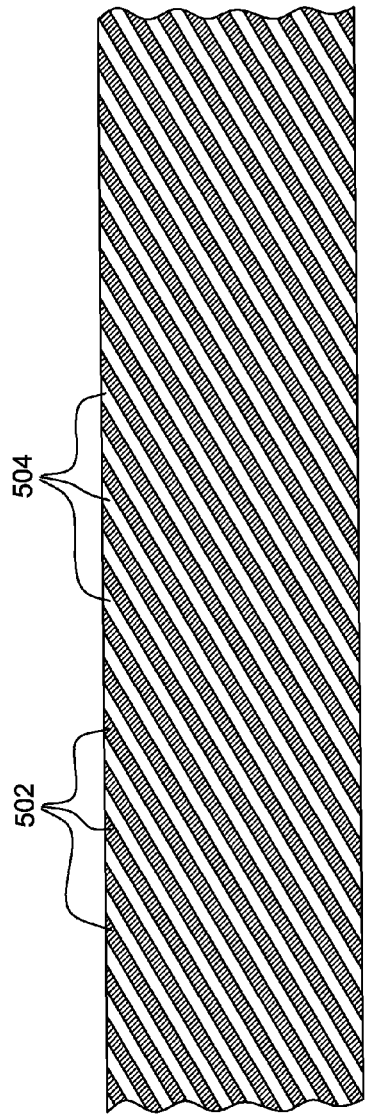
FIG. 5 depicts a set of angled ramps repeated in a pattern across a test object, in accordance with one or more aspects of the present invention.

FIG. 5 depicts a set of angled ramps repeated in a pattern across a test object, according to an aspect of the present invention. In this example, the set of angled ramps of FIG. 5 depicts a portion of the first set of angled ramps 412 depicted in FIG. 4C. In this embodiment, the set of angled ramps 502 are disposed parallel to each other and are spaced in a consistent pattern across the test object. This pattern may be defined by, for instance, a mathematical pattern. As described above, the set of angled ramps 502 may be surrounded in a solid cast by a cast material 504, such as a clear or semi-clear urethane described above. As noted above, ramps of the set of angled ramps 502 may have one or more characteristic that distinguish the set of angled ramps 502 from cast material 504 when imaged using a tomographic imaging device. For instance, the set of angled ramps 502 might have different signal absorption characteristics. In the case of a test object used in conjunction with CT tomographic imaging devices, the set of angled ramps 502 and cast material 504 may have different CT numbers to distinguish from one another in a tomographic slice image of the test object.

Figure 4D:
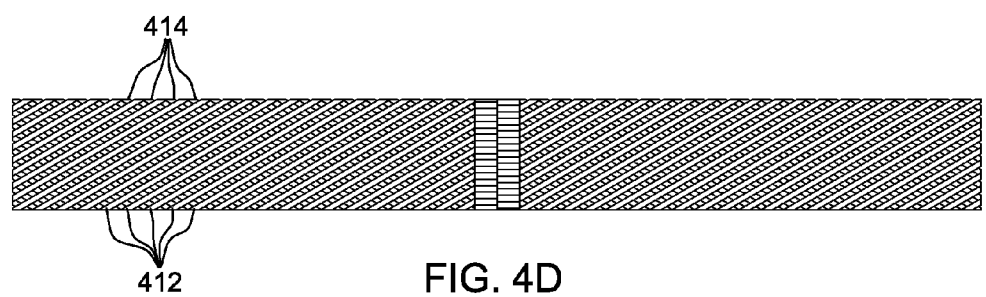

FIG. 4D depicts a side view of angled ramp structure 404 of FIGS. 4A-C. FIG. 4D shows a side view of the two sets of angled ramps of FIG. 4C, namely the first set of angled ramps 412 and the second set of angled ramps 414. The first set of angled ramps 412 are shown in the foreground and the second set of angled ramps 414 are depicted behind (in this view) the first set of angled ramps 412. This is further illustrated and described with reference to FIG. 6.

Figure 6:
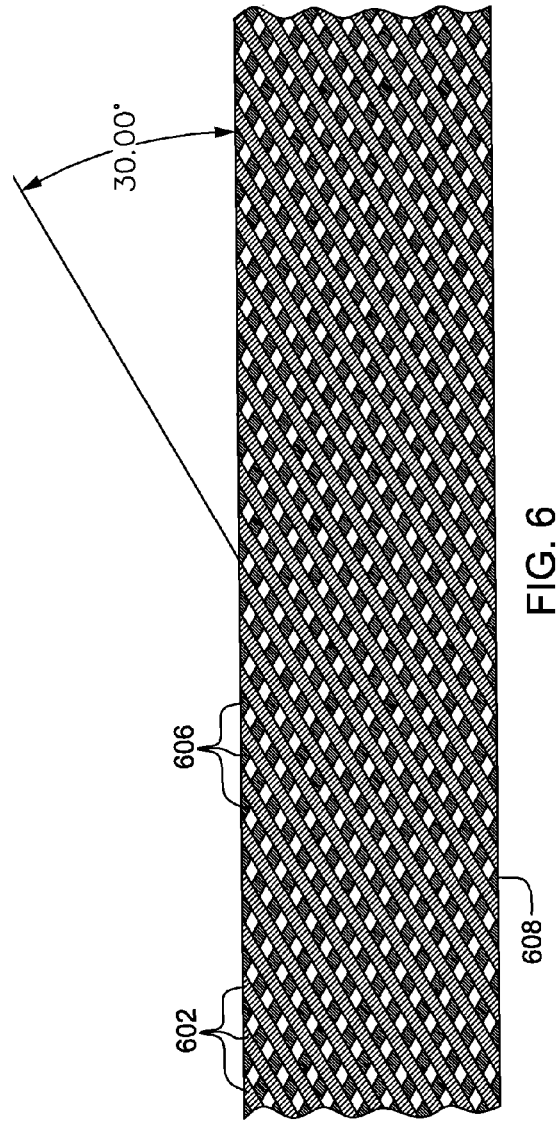
FIG. 6 depicts two sets of angled ramps of a test object, in accordance with one or more aspects of the present invention.

FIG. 6 depicts two sets of a plurality of angled ramps of a test object, in accordance with one or more aspects of the present invention. Presented therein is a partial side view of test object 400 of FIG. 4A. In FIG. 6, a first set of angled ramps 602 (light hashing) is shown in the foreground and a second set of angled ramps 606 (dark hashing) is shown behind the first set of angled ramps 602. As depicted, the first set of angled ramps 602 and the second set of angled ramps 606 may extend in opposing directions. For instance the first set of angled ramps 602 may extend toward the top right portion of FIG. 6 and the second set of angled ramps 606 may extend toward the top left portion of FIG. 6.

In one embodiment, a set of angled ramps may extend at a known angle away from a surface of the test object. In FIG. 6, the first set of angled ramps 602 extend away from a bottom surface 608 of the test object at an angle of 30 degrees from the bottom surface 608, as indicated. Additionally or alternatively, the second set of angled ramps 606 may extend an at angle away from bottom surface 608, for instance also at an angle of 30 degrees, but in an opposing direction relative to the first set of angled ramps 602, as noted above. The directions in which different sets of angled ramps of the angled ramp structure 404 extend relative to the bottom surface of the disc 402 can also be seen in FIG. 4A. It should be understood that the angular inclination of the sets of angular ramps may vary from that illustrated.

In accordance with an aspect of the present invention, a test object such as described above may produce a waveform profile when imaged using a tomographic imaging device. In one example, the angled ramps of a test object according to one or more aspects of the present invention are parallel and uniformly spaced from each other. Additionally, the angled ramps may be of equivalent thickness. In this manner, the angled ramps may be configured to produce a uniform waveform profile of pixel values of an image of the angled ramps, taken across the image of the angled ramps. That is, when the test object is imaged, a waveform profile across an image of a tomographic slice of the test object will produce a waveform profile that comprises a pattern of repeating signal values. A perfect image of a tomographic slice of the test object would produce a consistent pattern in the waveform profile taken across a set of angled ramps in the image, due to the consistent parallel spacing of the angled ramps as well as the consistent thickness of each angled ramp. However, due to inaccuracies and other imperfections in the spatial performance of a tomographic imaging device, a waveform profile taken across a set of angled ramps in an image may not yield a uniform waveform profile, in which case it is indicative of spatial distortion caused by the imaging device.

In another aspect of the invention, tomographic slice images of a test object according to aspects of the present invention, and the waveform profiles extracted therefrom, may be analyzed to evaluate performance of the tomographic imaging device. In one example, this analysis may be conducted through comparison to other waveform profiles, or through mathematical analysis of the data values of the waveform profile, or a combination of the two. For instance, actual waveform profiles extracted from an image may be analyzed and compared to a known configuration of the test object, such as the uniform waveform profile expected to be generated by the test object in an ideal imaging situation, or may be compared to other waveform profiles extracted from the image to evaluate performance of the tomographic imaging device.

The accuracy of the images generated by the tomographic imaging device can be evaluated to determine spatial imaging performance of the imaging device. Various characteristics of the waveform profile including, but not limited to, amplitude, frequency, and slope (rate of climb of the peaks), as well as associated mathematical analyses of the waveform profile, such as the associated Fourier transform, can be analyzed to determine and evaluate spatial performance of the tomographic imaging device. Spatial performance includes the device's ability to accurately image an object, including resolution characteristics and capabilities, as well as slice thickness, geometry, angular variation of the slice plane, and positioning across the scan field. If, for instance, there is a variation in slice thickness from one side of the slice to another, or if the slice is not flat, these variations will be reflected in an image of the test object, and the waveform profiles taken across the angled ramps in the image of the test object will encode these properties. A test object according to aspects of the present invention, therefore, may advantageously provide a single test object for evaluating numerous characteristics related to performance of the imaging device and characteristics of slice image generated therefrom.

In one embodiment, the waveform profiles extracted from the tomographic slice images may be visually analyzed. Visual analysis may, in some circumstance, be sufficient to provide a general evaluation of the performance of the imaging device. Alternatively or additionally, the waveform profiles may be mathematically analyzed, for instance automatically using processing units, such as processing unit 114 (FIG. 1) in communication with a tomographic imaging device. In one example, this mathematical analysis may be performed using one or more software programs executing on one or more processing units.

Figure 7A:
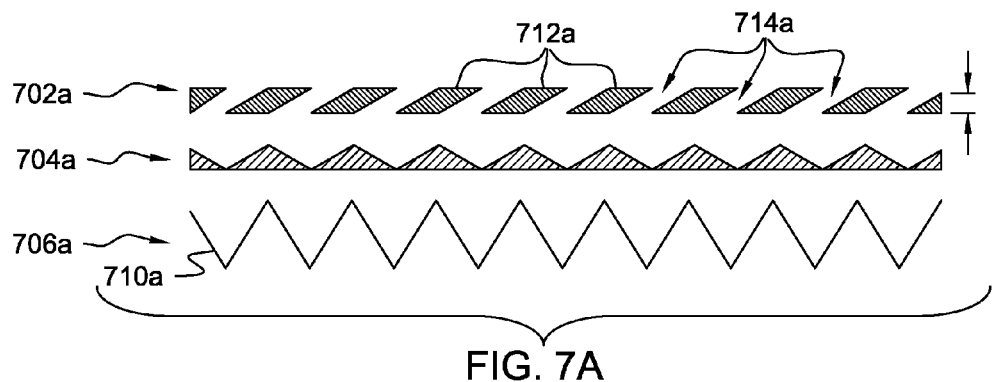
FIGS. 7A-7D each illustrate a side view of a tomographic slice of a test object and a corresponding waveform plot generated therefrom, in accordance with one or more aspects of the present invention.

To illustrate the concept that a waveform profile can encode analyzable characteristics of a tomographic imaging device, FIGS. 7A-7D each depict a side-view cross section of a slice of a test object in accordance with an aspect of the present invention, and a corresponding waveform generated therefrom. Referring to FIG. 7A, a side view of a tomographic slice 702a of the test object is depicted. The thickness of the slice is vertical in this picture. Slice 702a includes portions of angled ramps 712a separated by cast material 714a. The portions 712a comprise only portions of angled ramps of the test object, i.e. only those portions that are present in this particular slice. In other words, portions of angled ramps 712a represent portions of angled ramps of the test object which transcend the slice, i.e. are of such a length that they traverse the entire thickness of the slice 702a. Below slice 702a is a convolution 704a of the angled ramps of slice 702a. Convolution 704a represents an amount of interference, interaction, or absorption caused by the angled ramps 712a when it is scanned in a tomographic imaging device. For instance, in the case of CT using x-rays to scan the test object, 704a may represent an amount of absorption by the angled ramps 712a as the x-rays pass through the slice 702a (i.e. in the view of FIG. 7A, x-rays passing vertically through slice 702a from the top to the bottom of the slice). This concept is depicted and described in further detail below with reference to FIGS. 8A and 8B.

Continuing with FIG. 7A, 706a depicts a rescaled and normalized waveform plot of convolution 704a. For instance, in the case of CT, waveform plot 706a could represent a rescaled, normalized CT plot with any given point on the plot corresponding to the CT number associated with the corresponding point along the slice 702a.

Figure 7B:
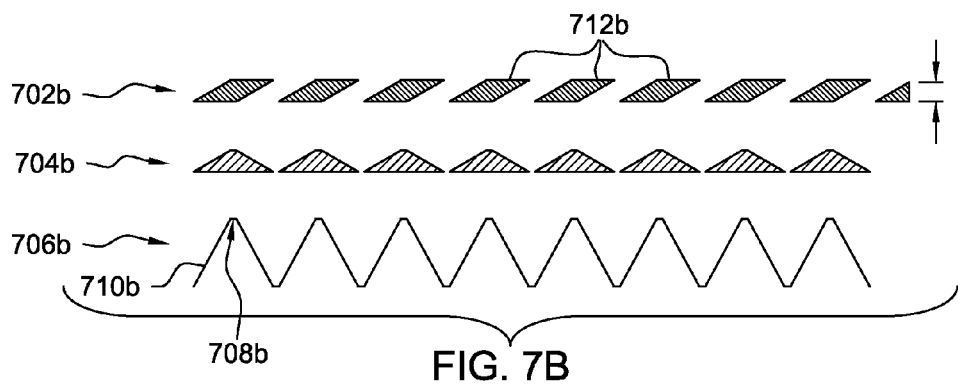
Figure 7C:
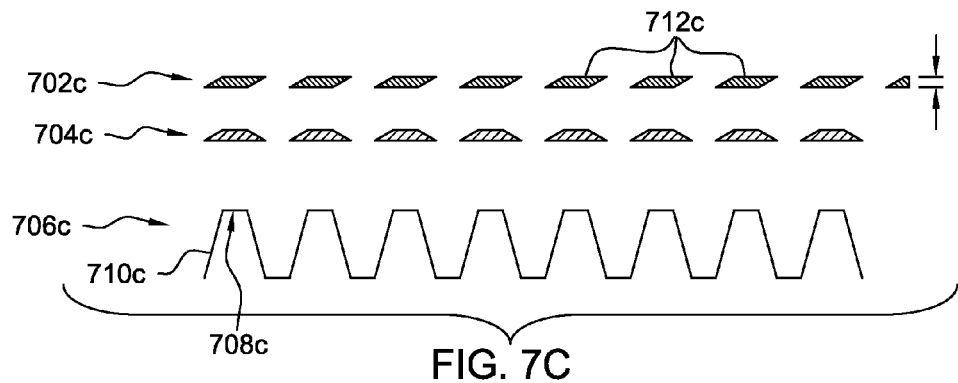
Figure 7D:
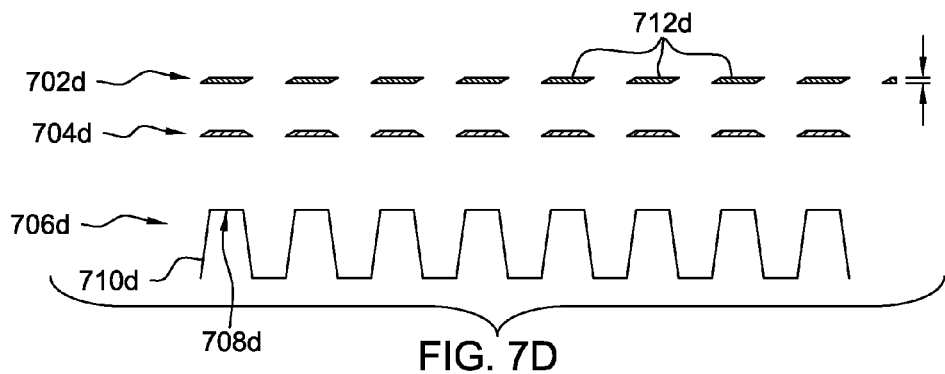

FIGS. 7B-7D depict similar slice and waveform profile characteristics as those depicted in FIG. 7A, but with varying slice thickness. Thickness of slices 702b, 702c, and 702d get progressively thinner, with 702d being thinner than 702c and 702c being thinner than 702b. As slice thickness decreases, the spacing between angled ramps in a slice (i.e. the space between each 712b, each 712c, or each 712d) grows relative to the thickness of the slice. A resulting gap between peaks of convolutions 704b, 704c, 704d (representing areas of no interference caused by the angular ramps) also grows. Additionally, a level of constant absorption by each angled ramp portion 712b, 712c, 712d creates plateaus 708b, 708c, and 708d, respectively, on the rescaled, normalized waveform plots 706b, 706c, and 706d. Further, slopes 710a, 710b, 710c, and 710d of plots 706a, 706b, 706c, and 706d, respectively, get steeper as slice thickness decreases. This is due to the fact that, as slice thickness decreases, the transition from minimum absorption (i.e. zero absorption, represented by the gaps between peaks in the convolutions) to maximum absorption (represented by the tops of the peaks in the convolutions) by the angled ramp portions occurs with lesser movement across the slice (left to right).

FIGS. 7A-7D illustrate that as slice thickness decreases, the shape of the corresponding waveform plot approaches what is known as a "square wave". A square wave is what would be obtained for the waveform plot in an infinitely thin slice. A true square wave has square edges, i.e. infinite ("undefined") slopes, and flat peaks. However, a waveform plot extracted from images obtained by a tomographic imaging device in accordance with aspects of the present invention exhibit a rounding and/or blurring characteristic into a repetitive sine-wave-like test pattern. The two major reasons are (i) the influence of finite z-slice thickness, and/or (ii) in-plane (x,y) point-spread function (or blur resolution limitations) of the imaging device. The former, i.e. z-axis slice thickness, was explained and illustrated above with reference to FIGS. 7A-7D. However, the waveform plots of FIGS. 7A-7D exhibit the same properties that would be observed had slice thickness been kept constant across FIGS. 7A-7D, but had in-plane resolution been varied across FIGS. 7A-7D. For instance, as resolution decreases, blurring increases, and the waveform plot will become more round, and exhibit less extreme sloping in the peaks/valleys of the waveform. In this manner, an image having infinitely great resolution will produce a square wave-shaped waveform plot (closer to that depicted in FIG. 7D), and as resolution decreases, blurring will produce a waveform plot closer to those depicted in FIGS. 7B and 7A. Thus, the waveform plot will actually encode both of these properties (and others).

Figure 8A:
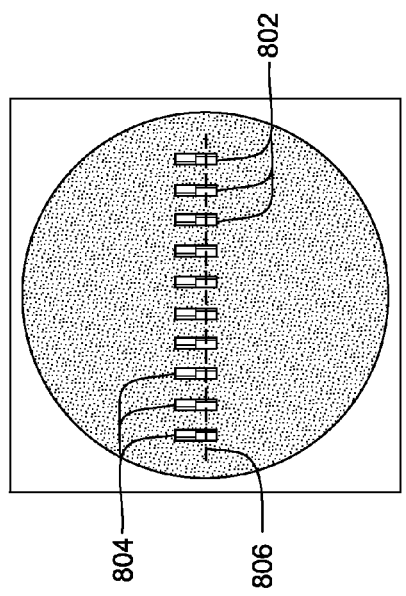
FIG. 8A depicts an image of a tomographic slice of a test object according to one or more aspects of the present invention.
Figure 8B:
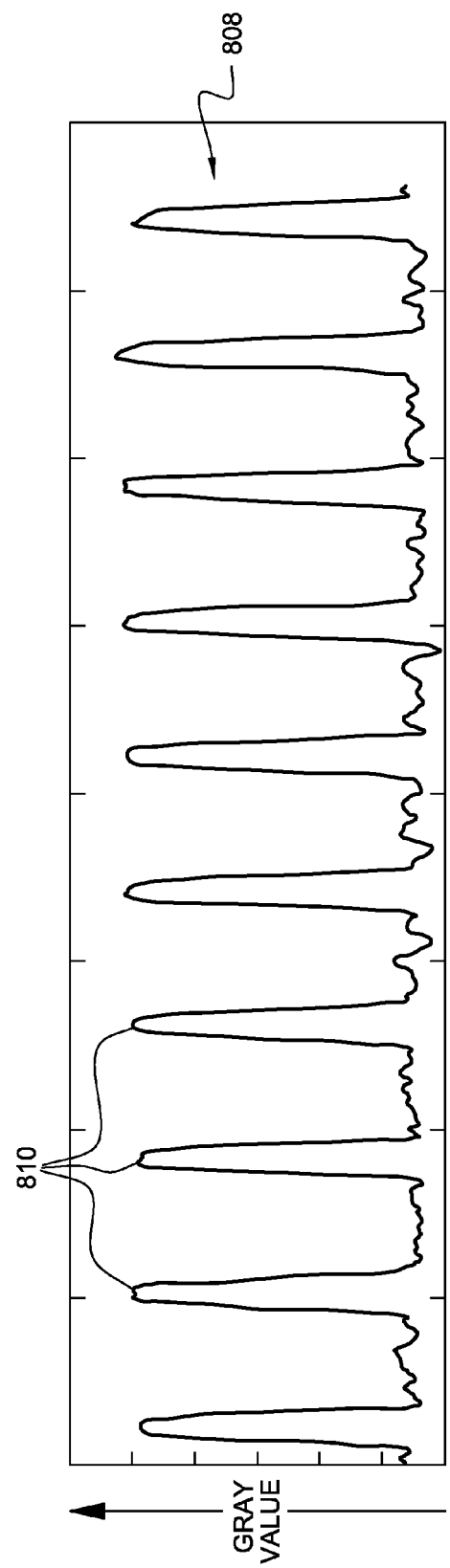
FIG. 8B depicts a waveform profile of a line across the image of the tomographic slice of FIG. 8A, in accordance with one or more aspects of the present invention.

FIGS. 8A and 8B illustrate the extraction of a waveform profile across a line taken across a tomographic slice image.

FIG. 8A depicts an image of a tomographic slice of a test object according to one or more aspects of the present invention. The view of FIG. 8A is typical of an image generated by a tomographic imaging device, the image having an x-y plane and an invisible z-axis dimension (extending away from the reader and into the paper). It is similar to the top view of FIG. 4C, except that FIG. 8A depicts only a tomographic slice, i.e. having a slice thickness (i.e. thickness in the z-axis) that is significantly smaller than a thickness of the test object of FIG. 4A.

FIG. 8A depicts a portion of a first set of angled ramps 802 and a portion of a second set of angled ramps 804 embedded in the solid cast material (stippled region) forming the disc portion of the test object. Also depicted in FIG. 8A is line 806, across which a waveform profile may be taken (described with reference to FIG. 8B) and analyzed in accordance with an aspect of the present invention.

FIG. 8B depicts a waveform profile taken across line 806 of FIG. 8A, which extends across the image of the tomographic slice in FIG. 8A. More specifically, the waveform profile represents gray values (in this example) obtained by moving across line 806 from left to right. In the case of CT, the gray values might be an indication of the CT number obtained at the corresponding point, as one having ordinary skill in the art would recognize. Peaks 810 of waveform profile 808 represent a point of maximum absorption caused by the potions 802 of the first set of angled ramps. The waveform profile may be derived from a plurality of pixel values taken across one or more ramps in the image of a tomographic slice of the test object. In the example of FIG. 8B, the waveform profile is derived from pixel values taken across each of the portions 802 of the first set of angled ramps.

As noted above, the waveform profiles taken across an image of a tomographic slice may be analyzed to evaluate spatial performance of the imaging device. One example of such an analysis is described with reference to FIGS. 9A and 9B. Those having ordinary skill in the art will recognize there are numerous other analyses that may be performed on the waveform profiles generated using a test object in accordance with one or more aspects of the present invention, as a method of evaluating performance of a tomographic imaging device.

Figure 9A:
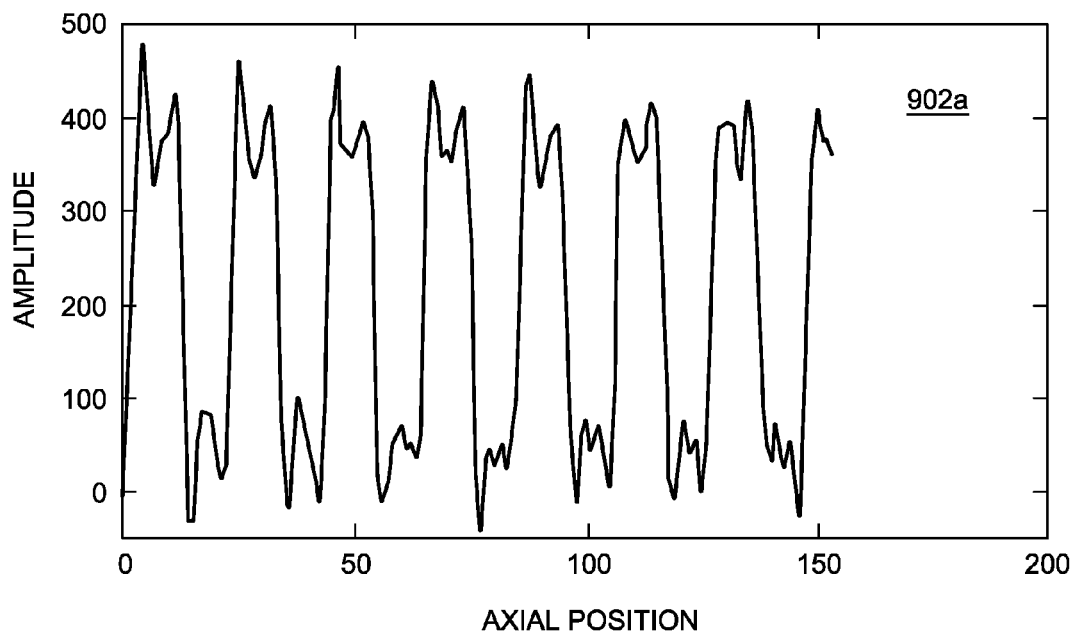
FIGS. 9A and 9B each depict a waveform profile generated from an image of a tomographic slice of a test object, and a corresponding Fourier transform generated therefrom, in accordance with one or more aspects of the present invention.
Figure 9A:
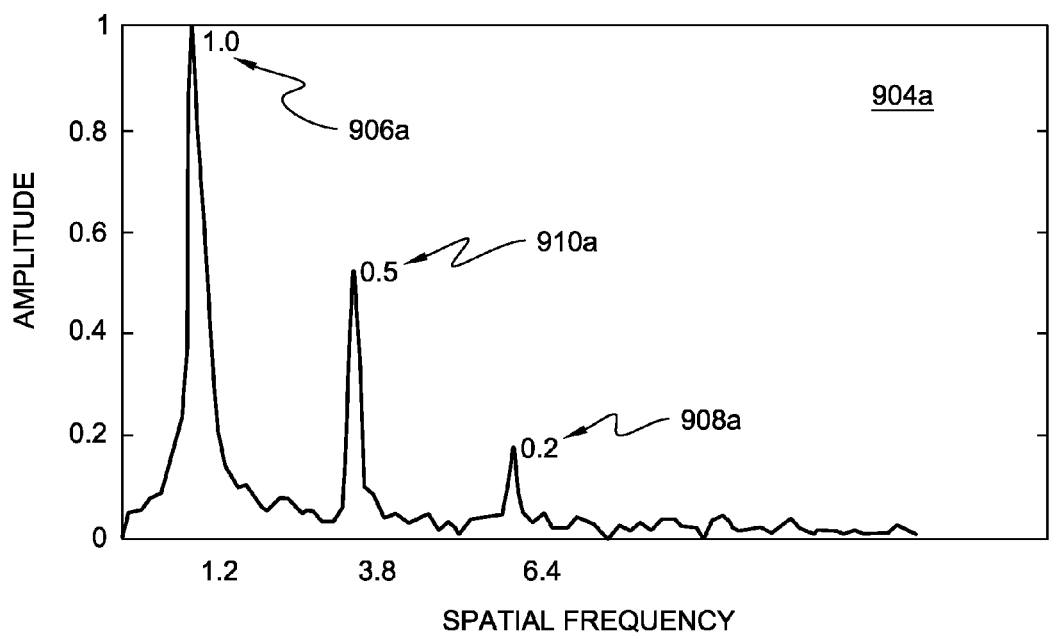
Figure 9B:
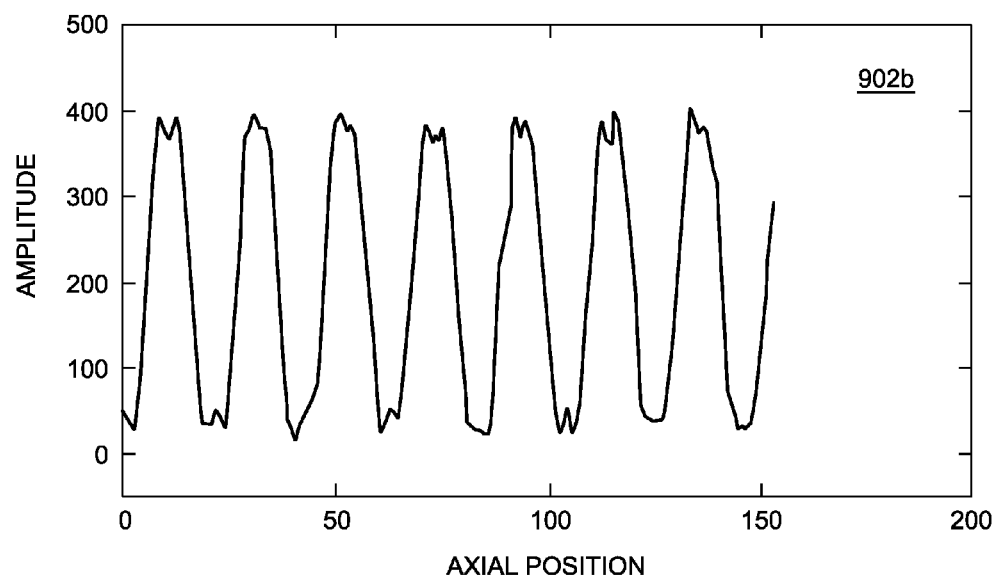
Figure 9B:
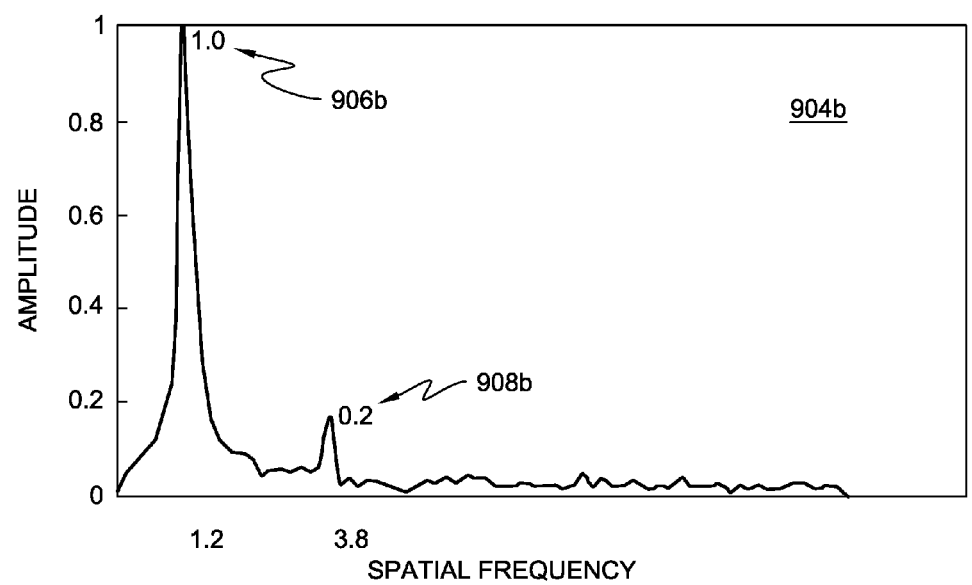

FIGS. 9A and 9B each depict a waveform profile generated from an image of a tomographic slice of a test object, and a corresponding Fourier transform generated therefrom, in accordance with one or more aspects of the present invention. For instance, FIG. 9A comprises waveform profile 902$a$, which forms generally a wave-shaped pattern similar to that of a sine-wave having jagged rises and falls, and comprises several peaks and valleys (not labeled). Depicted below waveform profile 902$a$ is a Fourier transform 904$a$ of the waveform profile 902$a$. As one having ordinary skill in the art would recognize, a Fourier transform is a decomposition of a signal into component frequencies, as utilized for instance when using a modulation transform function (MTF). Waveform profiles with a higher spatial repetition rate produce a higher level of spatial frequencies in the resulting Fourier transform, and consequently, the higher level of spatial frequencies will enable the observation of more harmonics in the Fourier transform. In the example of FIG. 9A, a visual inspection of Fourier transform 904$a$ of waveform profile 902$a$ reveals the clear presence of first harmonic 906$a$, second harmonic 910$a$, and third harmonic 908$a$.

FIG. 9B depicts another waveform profile 902$b$ and its corresponding Fourier transform 904$b$. However, as can be seen in FIG. 9B, Fourier transform 904$b$ of waveform profile 902$b$ reveals only two harmonics: harmonic 906$b$ and harmonic 910$b$. In this example, the second harmonic (the harmonic present between harmonics 906$b$ and 910$b$) of waveform profile 902$b$ has been reduced to near-zero amplitude and has disappeared, at least visually (although it mathematically still exists).

The waveform profile 902$a$ of FIG. 9A may be representative of a waveform profile taken from a thinner tomographic slice than that from which waveform profile 902$b$ of FIG. 9B is taken. This is evident from a mere visual inspection of the waveform profiles. As described above, characteristics of a waveform profile and its corresponding Fourier transform encode information about slice thickness, in addition to other information. Comparing waveform profile 902$a$ of FIG. 9A to waveform profile 902$b$ of FIG. 9B, we see that waveform profile 902$a$ is a relatively more oscillatory plot with waves having steeper rise and fall slopes and flatter peaks/valleys, whereas waveform profile 902$b$ is a plot with waves having more gradual slopes and rounder peaks and valleys. These characteristics mirror those described above with respect to the waveform plots of FIGS. 7A-7D, in which a waveform having flatter peaks and steeper slopes may be indicative of a thinner tomographic slice. Thus, just by visual inspection, assuming the same in-plane resolution is used in both cases, we can gauge relative thickness between the slice associated with FIG. 9A and the slice associated with FIG. 9B. In situations where the differences were not so pronounced, mathematical analysis of the data values of the waveform profiles 902$a$ and 902$b$ and Fourier transforms 904$a$ and 904$b$ could be performed to mathematically identify the presence of these and other differences.

The use of Fourier analysis, in this example, exploits well-known principles that periodic sampling points in an image plane produces corresponding periodic sampling points in the Fourier spatial frequency domain, thus resulting in "harmonics" in the Fourier transform plot. In this manner, if sampling points in the imaging plane occur at a fixed distance, the corresponding sampling points in the Fourier domain occur at integral multiples of reciprocal distance. Thus, it can be determined where peaks or harmonics occur and their amplitude measured, yielding information about slice thickness and/or in-plane resolution variations. Thus, for example, the peaks or harmonics (e.g. 904$a$, 904$b$) are found at multiples of reciprocal spacing distances of the wave periodicity. These repetitive sampling operations (typically referred to a "combs" or "Dirac sampling combs") result in corresponding Fourier domain "combs" which may be used in various analyses as one having ordinary skill in the art would recognize. Additionally, not only will harmonics of a Fourier transform provide information about spatial performance, but other properties of the Fourier transform will as well. For instance, as those having ordinary skill in the art would recognize, numerous types of analyses on a Fourier transform may be performed, including, but not limited to, analysis on area under the Fourier curve and/or under one or more harmonics thereof, peak amplitude, width, and height at various data points, etc.

Further, as described above, the Fourier transform encodes information about spatial resolution of the imaging device. As an example, properties of in-plane resolution become multiplicative in the spatial frequency domain (i.e. Fourier transform). A convolution (or blurring) due to resolution capabilities of the imaging device becomes a multiplicative filter (i.e. an MTF) in the spatial frequency domain. Thus, FIGS. 9A and 9B alternatively or additionally may represent the difference between a waveform profile taken from a lower resolution tomographic slice (FIG. 9B) versus a waveform profile taken from a higher resolution tomographic slice (FIG. 9A). In other words, tomographic slice image resolution will affect waveform profile and corresponding Fourier transform plots similarly to how slice thickness will so affect the plots.

Alternatively, the analysis of a waveform profile and/or a corresponding Fourier transform need not involve any such comparison to other waveform profiles and/or Fourier transforms. As one having ordinary skill in the art would recognize, a mathematical analysis of a single waveform profile or corresponding Fourier transform may indicate, for instance, exact slice thickness or in-plane resolution. Mathematically analyzing the degree of presence of the harmonics in the single Fourier transform, for example, may be used to determine slice thickness, presuming the in-plane resolution is known and/or can be taken into effect or deconvolved. Similarly, in-plane resolution may be determined if slice thickness is known or can be taken into effect. As noted, a waveform profile and Fourier transform will encode properties of both slice thickness and in-plane resolution. Thus, it may be useful to identify situations in which the influence of one or the other may be taken into account or factored-out. As an example, if it is known or can be determined that slice thickness is sufficiently thin as to impart such little relative impact on waveform profile and/or Fourier transform as compared to the impact of spatial resolution, then spatial resolution may be determined through an analysis of the profile and/or Fourier transform. Conversely, if spatial resolution is known or is so great that its effects on the waveform and corresponding Fourier transform is negligible, then slice thickness can be accurately determined.

In this regard, in one embodiment of the invention, analysis such as described above may be performed in conjunction with information provided through the use of other test objects, such as from one or more inserts 306 of FIG. 3. One or more inserts 306 may be utilized to provide one or more spatial performance characteristics that facilitate analysis of one or more waveform profiles and/or Fourier transforms extracted from images of the test object according to the present invention. For example, U.S. Pat. No. 5,164,978, issued Nov. 17, 1992 to Goodenough et al., describes a phantom insert usable to determine resolution of a tomographic imaging device. Analysis such as described above may, in one embodiment, take into account a characteristic, such as resolution, as determined by another test object, when analyzing the waveform profile(s) and/or Fourier transform(s) produced from imaging the test object according to the present invention. For instance, the Goodenough patent describes scanning a point spread function bead to determine an MTF. This MTF may then advantageously be used in conjunction with aspects of the present invention for instance in the analysis of the wave patterns in the waveform profile.

FIGS. 9A and 9B present an example of analysis that might be performed to mathematically identify properties of the tomographic slice to evaluate spatial performance of the imaging device. The waveform profile and the Fourier transform thus provide a visual and numerical way to analyze spatial performance of the imaging device.

In another embodiment of the present invention, analysis across multiple tomographic slices may be conducted to determine spatial performance of the tomographic imaging device in imaging a 3-dimensional volume. For instance, this analysis may be extended to 3-dimensional volume sets with nominally contiguous slices.

In yet a further embodiment, multiple waveform profiles may be taken across different portions of the image of the test object. For instance, a waveform profile may be taken across each of two opposing sets of sets of angled ramps and may then be compared with each other. In this manner, one waveform profile may serve as a reference to which the other waveform profile may be compared to identify consistencies and/or inconsistencies between two waveform profiles. For instance, their offset may indicate accuracy of slice position.

Figure 10:
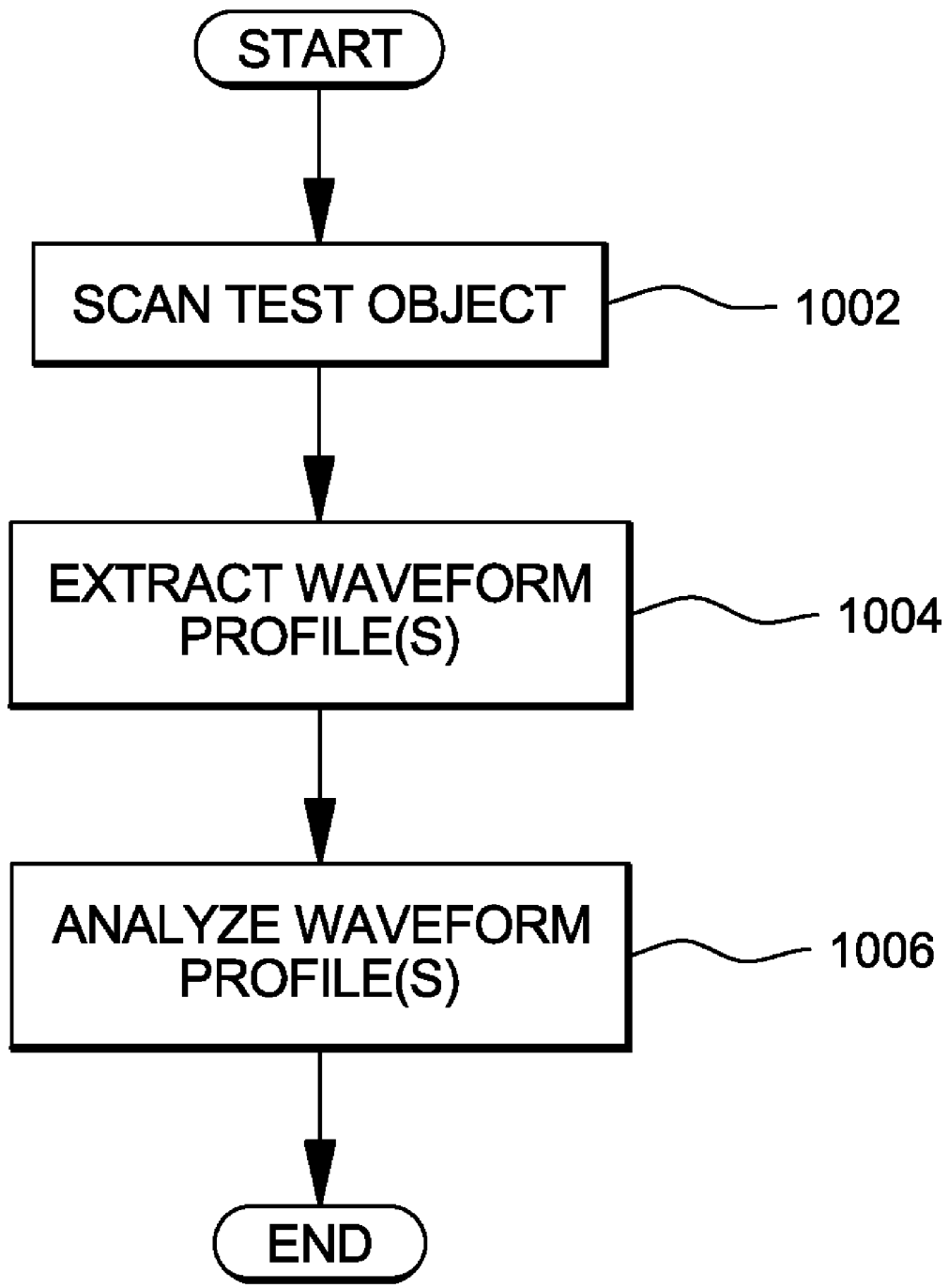
FIG. 10 depicts one method for evaluating performance of a tomographic imaging device, in accordance with one or more aspects of the present invention.

Thus, in accordance with an aspect of the present invention, a method is provided for evaluating performance of a tomographic imaging device. FIG. 10 depicts one example of such a method. In step 1002, a test object (such as a test object described above) is scanned using a tomographic imaging device. The scanning produces one or more images of one or more tomographic slices of the test object. In step 1004, one or more waveform profiles are extracted from across the one or more images. The one or more waveform profiles may then be analyzed, 1006, visually and/or mathematically to determine spatial performance of the tomographic imaging device, as described above. For instance, amplitude, frequency, and/or shape of the waveform profile may be analyzed to determine, for instance, tomographic slice geometry of one or more tomographic slices from which the one or more images were obtained.

In one embodiment, determined tomographic slice geometry may be compared to a known geometry of the test object in order to evaluate performance of the tomographic imaging device in scanning and imaging the test object. Additionally, or alternatively, a waveform profile extending across a first set of angled ramps of the image may be compared to a waveform profile extending across a second set of angled ramps of the image. For instance, in an image of a tomographic slice of test object 400 (FIG. 4A), a waveform profile taken across a line extending across the first set of angled ramps 412 (FIG. 4D) may be compared to a waveform profile taken across a line extending across the second set of angled ramps 414 (FIG. 4D) and compared to each other. As one example, an analysis of the two waveform profiles might show a flexion in the angled ramp structure as depicted in the image, for instance if one waveform is stretched relative to another. Flexion present in the image indicates deficiencies in the spatial performance of the imaging device.

As will be appreciated by one skilled in the art, aspects of the present invention may be embodied as a method and/or apparatus. In one example, a tomographic imaging device comprising a scanning device and a one or more data processing units may be provided, the scanning device for scanning a test object such as described above, and the one or more data processing units for extracting a waveform profile from an image of the test object and analyzing the waveform profile to determine spatial performance of the tomographic imaging device.

Aspects of the present invention are described herein with reference to flowchart illustrations and/or block diagrams of methods. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In one example, the computer program instructions could be embodied in data acquisition units 112 and/or one or more processing units 114 (FIG. 1) to provide a tomographic imaging device the capability of performing the method.

These computer program instructions may also be stored in a computer readable medium that can direct a computer, other programmable data processing units or apparatuses, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing units or apparatuses, or other devices to cause a series of operational steps to be performed on the computer, other programmable units or apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of methods, systems and other apparatuses according to various embodiments of the present invention. The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

Although embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A test object to facilitate evaluating performance of a tomographic imaging device, the test object comprising:
    a plurality of angled ramps repeated in a uniform pattern in at least one direction across the test object, wherein the plurality of angled ramps are configured to produce a uniform waveform profile across an image of a tomographic slice of the test object when imaged using the tomographic imaging device.

2. The test object of claim 1, wherein the plurality of angled ramps repeated across the test object are repeated according to a defined mathematical pattern.

3. The test object of claim 1, wherein the plurality of angled ramps comprise a first plurality of angled ramps repeated across the test object in a first direction and a second plurality of angled ramps repeated across the test object in a second direction.

4. The test object of claim 3, wherein the first direction is perpendicular to the second direction.

5. The test object of claim 1, wherein the plurality of angled ramps extend through at least a portion of the test object.

6. The test object of claim 5, wherein the plurality of angled ramps are parallel to each other.

7. The test object of claim 5, wherein the test object comprises a disc having a first surface and an opposing second surface, and wherein the plurality of angled ramps are embedded in the disc and extend away from at least one of the first surface or the second surface at a known angle.

8. The test object of claim 7, wherein the angled ramps extend away from at least one of the first surface or the second surface at an angle of approximately 30 degrees.

9. The test object of claim 1, wherein the waveform profile is taken along a line extending in the at least one direction across the test object.

10. The test object of claim 1, wherein the plurality of angled ramps comprise a first set of angled ramps and a second set of angled ramps extending in opposing directions relative to each other.

11. The test object of claim 10, wherein the first set of angled ramps are configured to produce a first uniform pixel value profile, and the second set of angled ramps are configured to produce a second uniform pixel value profile for comparison with the first uniform pixel value profile, the first uniform pixel value profile taken along a line extending across the first set of angled ramps, and the second uniform pixel value profile taken along a line extending across the second set of angled ramps.

12. A method for evaluating performance of a tomographic imaging device, the method comprising:
    scanning a test object using a tomographic imaging device to produce an image of a tomographic slice of the test object, the test object comprising a plurality of structures repeated in a pattern in at least one direction across the test object;
    extracting from the image of the tomographic slice a waveform profile of image values from multiple data points, the multiple data points extending across an image of the repeating pattern in the image of the tomographic slice; and
    analyzing the waveform profile of image values to determine spatial performance of the tomographic imaging device.

13. The method of claim 12, wherein the multiple data points comprise pixel values of the image of the tomographic slice.

14. The method of claim 12, wherein the analyzing comprises analyzing at least one of amplitude, spatial frequency, shape, and the presence of known harmonics of the waveform profile.

15. The method of claim 12, wherein the analyzing includes analyzing variation in in-plane (x-y) resolution.

16. The method of claim 12, wherein the analyzing comprises evaluating tomographic slice geometry to determine at least one of variation in slice thickness, and variation in slice surface geometry.

17. The method of claim 16, wherein the method further comprises comparing the evaluated tomographic slice geometry to a known geometry of the test object to evaluate the performance of the tomographic imaging device.

18. The method of claim 12, wherein the extracting further comprises extracting another waveform profile of image values from multiple other data points extending across the image of the tomographic slice, and wherein the analyzing comprises comparing the extracted waveform profile of image values with the extracted another waveform profile of image values.

19. The method of claim 12, wherein the method further comprises repeating the scanning, extracting, and analyzing of multiple other tomographic slices of the test object to evaluate performance of the tomographic imaging device when imaging a 3-dimensional volume set.

20. The method of claim 12, wherein the determining spatial performance comprises at least one of: determining variations in geometry of the tomographic slice, determining tomographic slice plane distortions, determining resolution capabilities of the tomographic imaging device, determining angular variation of the tomographic slice plane, and determining positioning across a scan field.

21. The method of claim 12, further comprising utilizing a determined spatial performance characteristic, determined at least in part by scanning another test object using the tomographic imaging device, to facilitate the analyzing the waveform profile of image values to determine spatial performance of the tomographic imaging device.

22. A tomographic imaging device comprising:
a scanning device; and
a data processing unit for:
    extracting a waveform profile of multiple data points from an image of a tomographic slice of a test object, the test object comprising a plurality of structures repeated in a uniform pattern in at least one direction across the test object and the plurality of structures configured to produce a uniform waveform profile across an image of a tomographic slice of the test object when imaged using the tomographic imaging device, wherein the multiple data points extend across the image of the repeating pattern in the image of the tomographic slice of the test object; and
    analyzing the waveform profile to determine spatial performance of the tomographic imaging device.

23. The tomographic imaging device of claim 22, in combination with a test object comprising a plurality of structures repeated in a uniform pattern in at least one direction across the test object, the plurality of structures configured to produce a uniform waveform profile across an image of a tomographic slice of the test object when imaged using the tomographic imaging device.

* * * * *